(12) United States Patent
Fischer et al.

(10) Patent No.: US 7,816,644 B2
(45) Date of Patent: Oct. 19, 2010

(54) PHOTOACTIVATED COLLISION INDUCED DISSOCIATION (PACID) (APPARATUS AND METHOD)

(75) Inventors: Steven M. Fischer, Hayward, CA (US); Harry F. Prest, Santa Cruz, CA (US); Robert Lee, Jr., Fremont, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1097 days.

(21) Appl. No.: 11/506,933

(22) Filed: Aug. 18, 2006

(65) Prior Publication Data

US 2008/0042056 A1 Feb. 21, 2008

(51) Int. Cl.
*H01J 49/26* (2006.01)
(52) U.S. Cl. ...................................... 250/288
(58) Field of Classification Search ............. 250/288
See application file for complete search history.

(56) References Cited

U.S. PATENT DOCUMENTS 5,073,713 A * 12/1991 Smith et al. ............... 250/282
6,828,549 B2 * 12/2004 Schweikhard et al. ....... 250/281
7,429,728 B2 * 9/2008 Enke .......................... 250/282

* cited by examiner

*Primary Examiner*—Kiet T Nguyen (57) ABSTRACT

The invention provides a system apparatus and methods for fragmenting various molecules. In particular, the invention may be employed for fragmenting biomolecules like peptides to determine sequence information. The invention provides a mass spectrometry system for photo-activated collision induced dissociation. The mass spectrometry system or device includes an ion source for producing ions, a photon source adjacent to the ion source for photo-activating ions produced by the ion source, an electrical element adjacent to the photon source for creating an electric field for accelerating ions produced by the ion source and photo-activated by the photon source; wherein ions are produced by the ion source, photo-activated by the photon source and accelerated into a surface to cause dissociation of the activated ions; and a detector downstream from the ion source for detecting the collision induced and dissociated ions.

45 Claims, 5 Drawing Sheets

PHOTOACTIVATED COLLISION INDUCED DISSOCIATION (PACID) (APPARATUS AND METHOD)

BACKGROUND

Ascertaining the structure and function of various biochemical and nonbiochemical molecules and materials is becoming increasingly important to chemists and biochemists alike. With the development of new areas of research, novel, efficient and effective analysis and measurement tools are in high demand. For instance, with increasing developments in proteomics, new techniques are being developed and designed each day for sequencing and ascertaining primary structure of proteins and peptides. Although there are a number of techniques to do this, none are as precise, efficient and effective as mass spectrometry.

Ascertaining the amino acid sequence of a peptide is an important task because the amino acid sequence of the peptide or protein often determines higher order structure as well as function. In addition, the peptide structure can be used to search protein databases to determine where the peptide originated from. Since peptides can be quite large, oftentimes these molecules are fragmented by mass spectrometry techniques and the resulting abundance and sequence data can later be determined or de-convoluted with the help of libraries. It is ideal for fragmentation to occur at all the amide bonds in the peptide backbone such that a /b-series or y-series is generated. This greatly aids sequence interpretation. Presently, there are a number of techniques for performing fragmentation of molecules in mass spectrometry systems. Each of these methods suffers from some limitations.

Collision induced dissociation (CID) is a technique in which a peptide or other molecule is accelerated into a gas and is fragmented by collisions with the gas molecules. CID is limited in the sense that it does not allow specificity in the fragmentation of certain bonds. There are no electronic transitions in the molecules to be fragmented and only gas may be employed with the collisions. The technique is generally effective for fragmenting different molecules, but provides limited specificity in the case of peptides.

Infrared photo-dissociation (IRPD) is another fragmentation technique which employs infrared photons to excite the translational, rotational and vibrational bonds of molecules. The technique is effective in providing information regarding various molecules, structures and bonds. However, since there are no electronic transitions, the technique is generally ineffective in fragmenting peptides or other molecules along specific bonds. No gas is used with this technique. Long wavelengths are employed to fragment molecules.

Surface induced dissociation (SID) is a technique that accelerates the molecule or peptide into a surface. The technique does not require a gas and the fragmentation of bonds is non-specific.

Electron capture dissociation (ECD) is another technique known and used in the art. This technique works by capturing an electron on the surface of charged molecules. In other words, EDC occurs wherein dissociation of the analyte molecules and ions results from attachment of low energy electrons. This technique provides non-specific bond fragmentation. The technique is limited, however, in that it only works on multiple charged ions and only in the positive mode.

Electron transfer dissociation (ETD) is the newest technique now being heavily used to study molecules. In this technique, a thermal electron is transferred from a negative ion to the analyte ion as a means of transferring energy to destabilize the ions. This technique was designed and developed particularly for peptide fragmentation. It is effective in providing simple fragmentation patterns that are easily understandable. The technique is limited, however, in that it only works on multiple charged ions and only in the positive mode.

In summary, there is a need for an apparatus and method to efficiently, effectively and accurately fragment different molecules for mass spectrometry analysis. In addition, there is a need to be able to fragment peptides at bond specific points for quick, efficient and easy determination of amino acid sequences. These and other problems are addressed by the present invention.

SUMMARY OF THE INVENTION

The invention provides a mass spectrometry system for photo-activated collision induced dissociation (PACID), comprising an ion source for producing ions, a photon source adjacent to the ion source for photo-activating ions produced by the ion source, an electrical element adjacent to the photon source for creating an electric field for accelerating ions produced by the ion source and photo-activated by the photon source, wherein ions are produced by the ion source, photo-activated by the photon source and accelerated into a surface to cause dissociation of the activated ions; and a detector downstream from the ion source for detecting the collision induced and dissociated ions.

The invention provides a device for photo-activated collision induced dissociation, comprising an ion source for producing ions, a photon source adjacent to the ion source for photo-activating ions produced by the ion source, and an electrical element adjacent to the photon source for creating an electric field for accelerating ions produced by the ion source and photo-activated by the photon source, wherein ions are produced by the ion source, photo-activated by the photon source and accelerated into a surface to cause collision induced dissociation of the activated ions.

The invention also provides a method for photo-activated collision induced dissociation. The method comprises providing ions, photo-activating the ions to a higher energy state, accelerating the ions, and colliding the ions with a surface to cause them to dissociate at certain preferred bonds.

BRIEF DESCRIPTION OF THE FIGURES

The invention is described in detail below with reference to the following figures.

DETAILED DESCRIPTION OF THE INVENTION

Before describing the invention in detail, it must be noted that, as used in this specification and the appended claims, the singular forms "a," "an," and "the" include plural referents unless the context clearly dictates otherwise. Thus, for example, reference to "a housing" may include more than one "housing", reference to "an electrical element" may include more than one "electrical element".

In describing and claiming the present invention, the following terminology will be used in accordance with the definitions set out below.

The term "adjacent" means near, next to, or adjoining.

The term "collision induced dissociation" refers to the technique of colliding a molecule with the surface of one or more gas molecules and/or planar surfaces to cause the molecules to split at particular bonds. This technique typically produces ion fragments that may be determined and characterized by mass to charge (m/z) ratios in a mass spectrometry system.

The term "ion source" uses its common meaning in the art. The term includes any ion sources that may be used to produce ions. This may include and not be limited to known ion sources in the art. For instance, some ion sources may include and not be limited to atmospheric pressure photoionization (APPI) ion sources, atmospheric pressure chemical ionization (APCI) ion sources, electrospray ionization (ESI) ion source, chemical ionization (CI) ion sources, matrix assisted laser desorption ionization (MALDI) ion sources, atmospheric pressure matrix assisted laser desorption ionization (AP-MALDI) ion sources etc. Ion sources may be employed at ambient temperature, or above or below atmospheric pressure. Atmospheric pressure is defined at around 760 Torr or 1 atmosphere. Devices below atmospheric pressure are generally under vacuum.

The term "photon source" refers to any source used to produce photons for irradiating a sample or analyte.

The term "electrical element" refers to a device for creating an electric field. In some embodiments this may include one or more electrodes. The term has broad based meaning to include any number of devices with associated parts and/or software that use or create electric field or fields for accelerating ions.

The term "surface" refers to any area that is capable of causing collisions and/or fragmentation of molecules. For example a "surface" may comprise a portion of a gas molecule or a portion of a device such as a planar surface.

Figure 1:
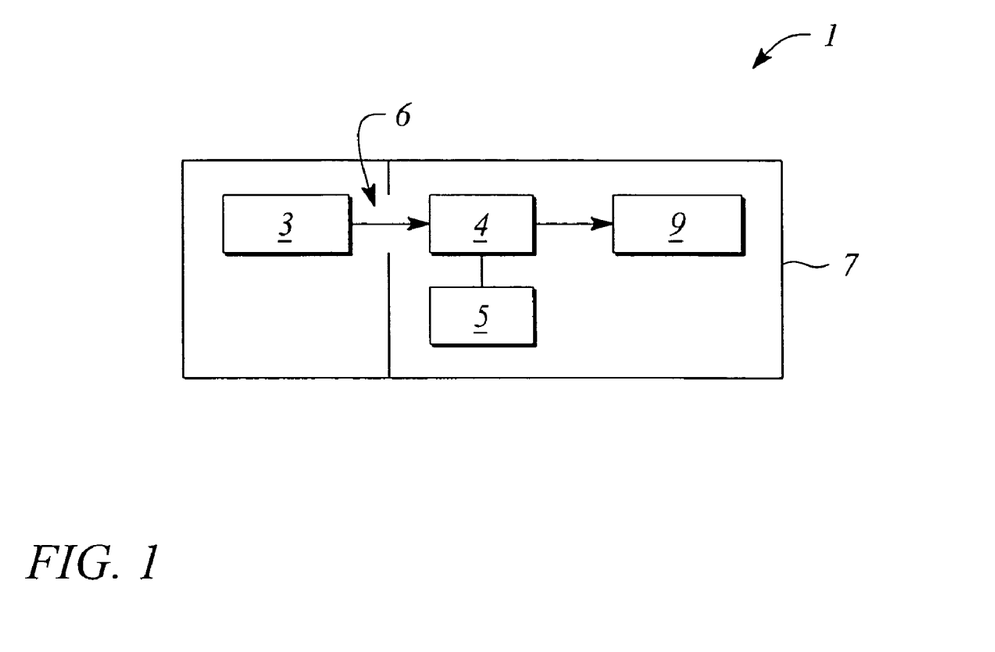
FIG. 1 shows a general block diagram of the present invention.

FIG. 1 shows a general block diagram of the present invention. The figures are not to scale and are used for illustrative purposes only. They should not be interpreted to limit the broad scope of the invention. The mass spectrometry system 1 of the present invention comprises an ion source 3, a photon source 4, an electrical element 5 and a detector 9. Optional ion optics 6 may be employed with the present invention. Ideally, optional ion optics 6 may be employed between the ion source 3 and the detector 9. Electrical element 5 is in electrical connection with photon source 4. An optional housing 7 may be employed for enclosing the ion source 3, photon source 4 and/or detector 9. It should be noted that the present invention may comprise a separate device for photoactivated dissociation or be used in a mass spectrometry system. Other devices arrangements and designs not disclosed or discussed may also be possible.

The ion source 3 may comprise any number of ion sources known or used in the art for producing ions. For instance, the ion source 3 may comprise electron impact (EI), photo ionization (PI), electrospray ionization (ESI), chemical ionization (CI), a matrix assisted laser desorption ionization (MALDI), an atmospheric pressure matrix assisted laser desorption ionization (AP-MALDI) source, a fast atom bombardment ion source, and an atmospheric pressure photoionization (APPI) source. Other ion sources known in the art and not discussed may also be employed with the present invention. The invention should not be interpreted to be limited to the disclosed ion sources.

The photon source 4 is disposed adjacent to the ion source 3. The photon source 4 may comprise any number of photon sources 4 that can excite and/or irradiate ionized sample molecules. The photon source 4 may be designed to irradiate in the ultraviolet and/or visible light ranges. For instance, the wavelengths produced may range from 190-900 nm in wavelength. Ideally, the photon source 4 can be placed anywhere in the mass spectrometry system 1. In addition, the photon source 4 may be capable of being focused on limited excitation ranges to enhance or maximize selectivity. For instance, it may comprise a filter, laser, monochrometer, or any other device that may enhance selective bond excitation by the selection of a limited range of photon wavelengths in a defined range. However, it is a requirement of the invention that the photon source 4 be in such an arrangement that the ions produced by the ion source 3 may be excited and retained at higher energy states for collision with a surface while in the excited state. In certain embodiments a collision gas may be employed. In other embodiments of the invention a planar surface may be employed. In other words, the collision surface must be disposed in a position in which it can fragment the ions that collide with it.

The electrical element 5 is disposed adjacent to the photon source 4. The electrical element 5 may comprise one or more electrodes for accelerating ions into the surface for collisions. Ideally, the electrical element is disposed adjacent to the ion source 3 and photon source 4. The ions may be first accelerated and irradiated by the photon source 4 and/or irradiated by the photon source 4 and then accelerated. This is not important to the invention. What is important is that the ions are accelerated and in excited states prior to collision with the surface (See FIG. 9). The collisions at high speed and excited states allow for the fragmentation of the ions along particular bonds. The electrical element 5 may also comprise one or more, wires, leads, logic devices/controllers and output screens and/or software for determining and/or setting the magnitude, time, wavelengths and field strength of the electrodes. The electrodes and/or electrical element 5 should be capable of providing enough voltage to create an acceleration field. Typically, this would mean maintaining a voltage of from about 0-1000 volts.

The detector 9 is disposed downstream from the photon source 4. Any number of detectors may be employed with the present invention. For instance, the detector may comprise a Q-TOF, time-of-flight (TOF) or ion trap type device. Other detectors known in the art may also be employed. It is also within the scope of the invention that other MS, devices and or fragmentation chambers may be employed in tandem with the present invention. For instance, other collision cells to perform ECD, ETD, CID and PQD may also be employed with the present invention.

Referring now generally to FIGS. 2-7, the present invention will now be discussed in more detail.

Figure 2:
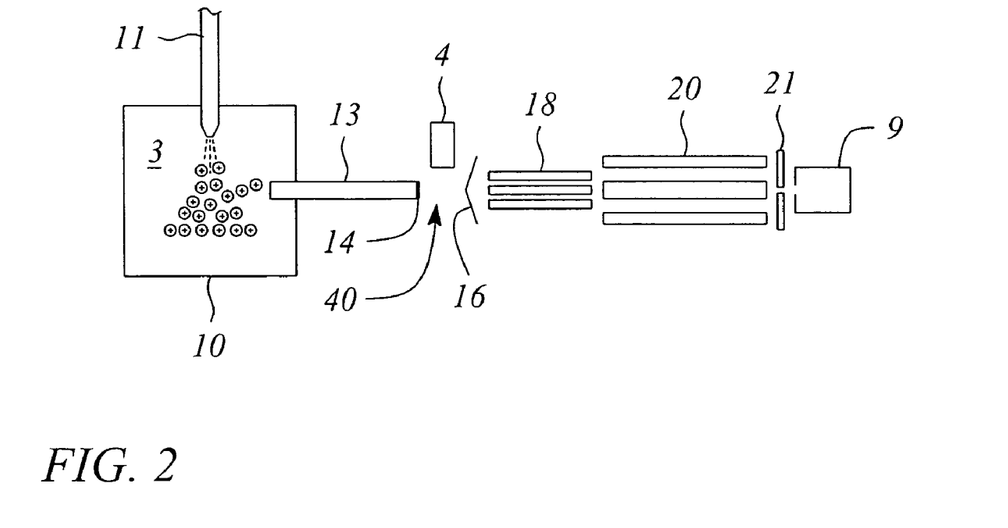
FIG. 2 shows a first embodiment of the present invention in MS mode.

FIG. 2 shows a first embodiment of the present invention in single MS mode. The figure shows an ion source 3 enclosed in an optional housing 10. An optional nebulizer tip 11 is also shown releasing ions into a capillary 13. In this embodiment of the invention electrical element 5 comprises one or more electrodes (as will be discussed later). For instance, a first electrode 14 is positioned adjacent to the exit end of the capillary 13. It should be noted that the electrical element 5 may comprise a separate or integrated structure with capillary 13 (note that electrical element 5 is not labeled in FIG. 2 since it comprises first electrode 14. Please refer to FIG. 1 for clarification).

A skimmer 16 is positioned downstream from the first electrode 14. An optional ion guide 18 may also be employed before the mass spectrometer 20. Ion guide 18 is employed for moving and directing ions into the mass spectrometer 20. The mass spectrometer 20 may comprise a mass filter or ion guide. In the present embodiment of the invention a quadrupole mass filter is shown. Other devices known in the art may be employed. For instance, a hexapole, an octapole, and other multipole/multiple rod structures known in the art may be employed. In this embodiment of the invention the photon source 4 is disposed between the first electrode 14 and the skimmer 16. First electrode 14 is used for accelerating ions from the capillary 13 toward the ion guide 18 and/or first mass spectrometer 20. The skimmer 16 operates to remove neutral molecules or similar type ions that cause interference with the mass spectrometer readings. It should be noted that the region between the first electrode 14 and the skimmer 16 shown as reference numeral 40 defines an area where background gas from the source may collect. This excess gas resides in this area and may be removed by an optional vacuum (not shown in figures). This excess gas is important to the invention since it may be used for the surface and collisions discussed earlier. The gas may comprise any gases known and used in the art. Nitrogen is one example of such a gas. Other gases such as helium, air, argon, hydrogen etc. that are known and used in the art may be employed. Optional ion optics 21 may be employed between the mass spectrometer 20 and the ion detector 9. The optional ion optics 21 may be employed for moving, directing or transporting ions.

Figure 3:
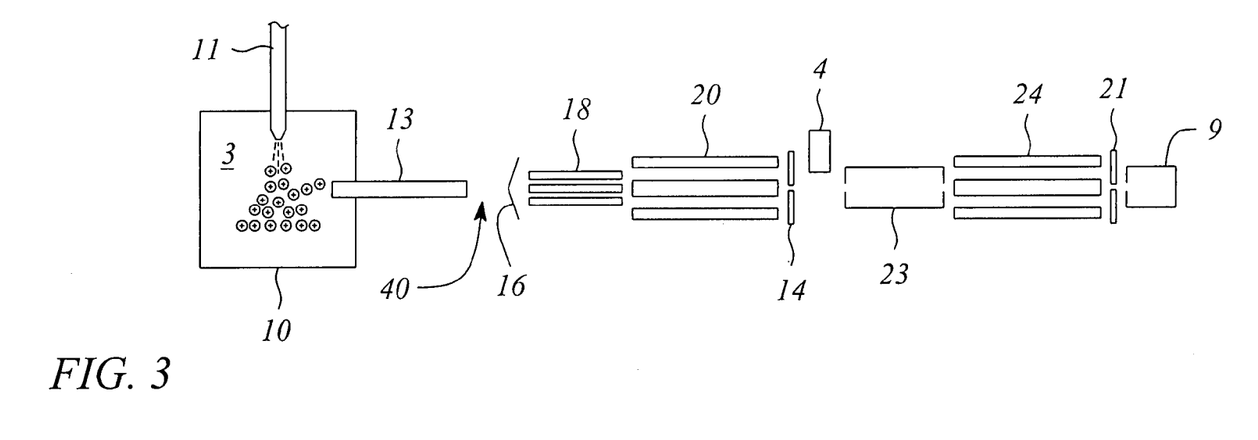
FIG. 3 shows a second embodiment of the present invention in MS/MS mode.

FIG. 3 shows a second embodiment of the present invention in MS/MS mode. This embodiment of the invention is similar to FIG. 2. However, in this embodiment of the invention the first electrode 14 is dispose adjacent to the photon source 4 and interposed between a first mass spectrometer 20 and second mass spectrometer 24. A collision cell 23 is disposed adjacent to the photon source 4. The collision cell 23 is employed for fragmenting and/or confining/transporting molecules before they enter the second mass spectrometer 24.

Figure 4:
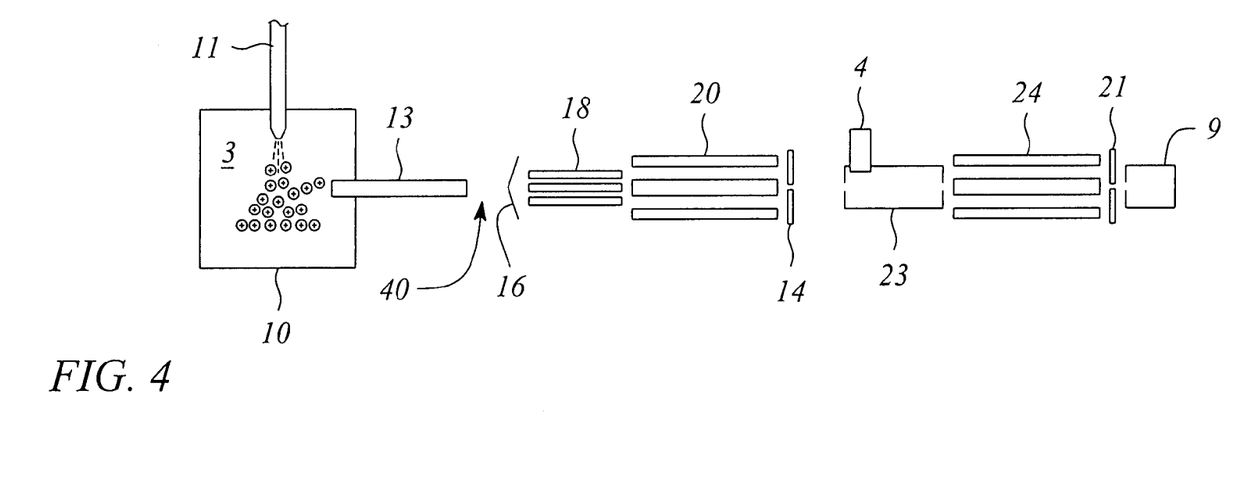
FIG. 4 shows a third embodiment of the invention in MS/MS mode with lamp in collision cell.

FIG. 4 shows a similar embodiment of the invention to FIG. 3, but the photon source 4 is disposed in or in contact with the collision cell 23.

Figure 5:
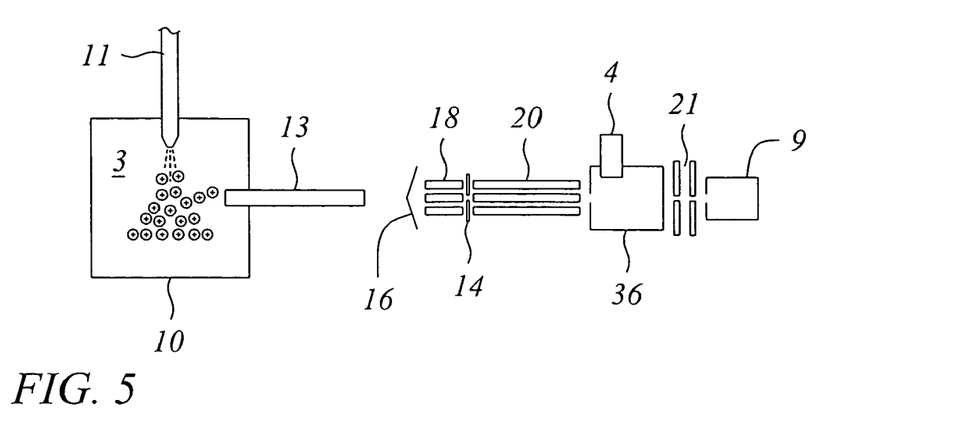
FIG. 5 shows a fourth embodiment of the invention with an MS trap.

FIG. 5 shows a similar embodiment of the invention to FIG. 4, but an ion trap 36 is employed with the present invention. In addition, the photon source 4 is disposed in the ion trap 36. It should be noted that the photon source 4 need not be disposed in the ion trap 36. For instance, in other embodiments of the invention it is anticipated that the photon source 4 may be disposed adjacent to the ion trap 36. Ion optics 21 may be employed downstream from the ion trap 36 before the detector 9.

Figure 6:
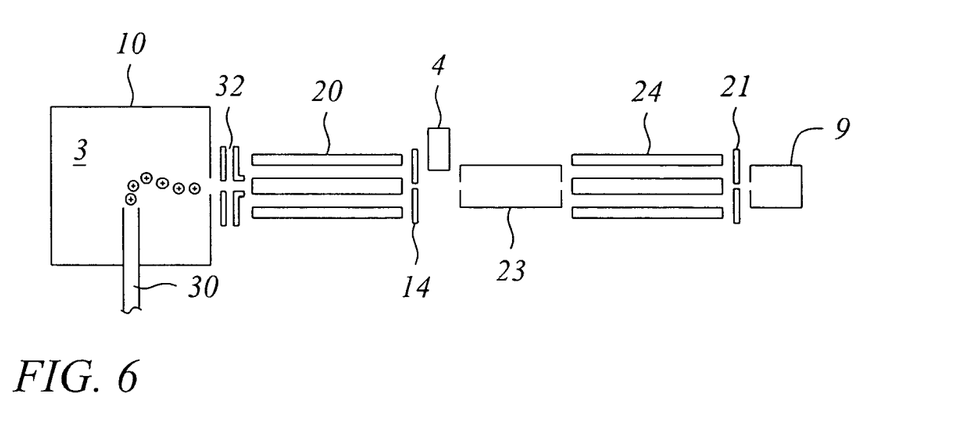
FIG. 6 shows a fifth embodiment of the present invention showing GC MS/MS mode.

FIG. 6 shows a similar embodiment of the invention to FIGS. 2-5. However, this embodiment of the invention shows the present invention in GC MS/MS mode. It should also be noted for simplicity the present invention is shown in MS/MS mode. This should not be interpreted to limit the present invention. For instance, the present invention may also be employed in single MS mode. In GC MS mode and GC MS/MS mode an ion source 3 is employed. A housing 10 is employed in which a GC column 30 is employed. Ion optics 32 is employed adjacent to the housing 10 and exit end of the column 30. This embodiment of the invention employs a photon source 4 and collision cell 23 disposed between a first mass spectrometer 20 and the second mass spectrometer 24. Other embodiments and arrangements of the invention may also be possible. It should be noted that the invention should not be interpreted to be limited to these disclosed arrangements or configurations.

Figure 7:
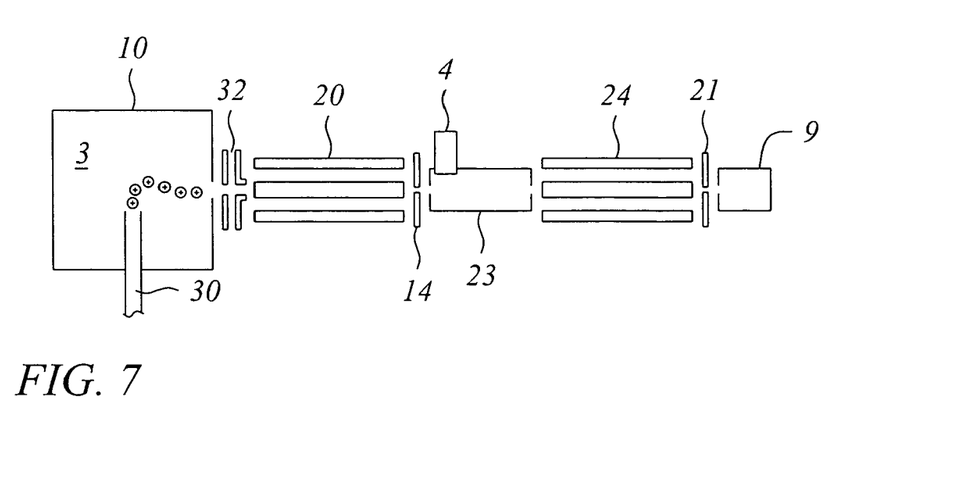
FIG. 7 shows a sixth embodiment of the present invention showing GC MS/MS with lamp in collision cell.

FIG. 7 shows a sixth embodiment of the present invention. This embodiment of the invention is similar to FIG. 6, but the photon source 4 is disposed in the collision cell 23. In the GC MS and GC MS/MS embodiments the entire system can be enclosed in a single housing (not shown). For instance, the ion source 3, the photon source 4, the ion optics 6 and the detector 9 may all be in the same housing 7. The housing 7 may be maintained under vacuum (see FIG. 1 for further clarification on the housing).

In contrast, in the embodiment of the invention that are used for LC MS or LC MS/MS the ion source 3 may be separated from the other components. The ion source 3 may be maintained at atmospheric pressure while the remainder of the instrument and/or components may be maintained under vacuum.

FIGS. 3-4 and 6-7 show embodiments of the present invention where a collision cell 23 and collision gas are employed with the present invention to promote fragmentation of the sample. In most cases, the collision gas may comprise nitrogen, argon or helium. Other gases known in the art may also be employed with the present invention. For instance, in certain instances the collision gas may be air or a mixture of gases. The invention should not be interpreted to be limited to the present embodiment. Other chambers and/or gases may be employed to create fragmentation.

As discussed, a collision cell 23 may not be the only structure used to fragment ions or molecules. For instance, a planar surface may also be provided to cause ion fragmentation (See FIGS. 2 and 5). Other embodiments and/or positions of the planar surface may be employed to increase or create the fragmentation. The planar surface may comprise any number of orientations, shapes, sizes and/or thicknesses.

Having described the apparatus of the invention, a description of the method is now in order. The invention provides a method for photo-activated collision induced dissociation, comprising providing ions, photo-activating the ions to a higher energy state, accelerating the ions, and colliding the ions with a surface to cause them to dissociate at certain preferred bonds.

Referring generally to FIGS. 1-9, the method of the invention begins by the introduction of a sample into the mass spectrometry system 1 or device for photo-activated collision induced dissociation. The analyte is then ionized by the ion source 3. After having been ionized in the ion source 3, the analyte is then directed toward the photon source 4. The photon source 4 is adjacent to the ion source 3. In particular, optional ion optics 6 may be employed for directing the ions further downstream. The ions then are subjected to irradiation by the photon source 4 and/or acceleration by the electrical element 5. The electrical element 5 may first accelerate the ions and they may then be irradiated by the photon source 4 into excited states. It is also possible that the ions may first be accelerated. It is important to the invention that the ions be both accelerated and in an excited state when they are collided with a gas or planar surface (See FIGS. 4, 5 and 9). After the ions are fragmented they are passed downstream to a detector 9 which is used for detecting the ion fragments.

Referring now to FIG. 2 a detailed description of the method of the invention will now be provided. As discussed, ions are produced in the ion source 3 and then enter the capillary 13. The ions are then directed through the capillary and pass by the photon source 4 and first electrode 14. The photon source 4 irradiates the molecules and the first electrode 14 provides an electric field for accelerating them. The ions may be accelerated and then irradiated or vice versa. It is important to the invention that the ions are both accelerated and in excited states when they are collided against a surface or gas. In FIG. 2 the ambient case in or adjacent to region 40 may be employed for causing fragmentation of the ions. The ion guide 18 then collects the ions and passes them onto first mass spectrometer 20. The ions are then separated by mass to charge ratios and then directed to a detector 9 by assistance of optional ion optics 21.

FIG. 3 shows an MS/MS mode arrangement. In this embodiment of the invention a collision cell 23 is employed instead of a planar surface. In this embodiment of the invention the ions are fragmented using a gas in the collision cell 23. As describe above the photon source 4 is used to irradiate the ions and excite them to higher energy states before they strike the gas molecules in the collision cell 23. FIG. 4 shows a similar arrangement and method, but the ions are irradiated by the photon source 4 when they are inside the collision cell 23.

FIG. 5 shows a method of the invention which employs an ion trap 36. As discussed above, ions are produced by the ion source 3 and then collected by the capillary 13. They are then passed through the skimmer 16. They then pass through the ion guide 18 where they are then directed through the first electrode 14 and first mass spectrometer 20. The ions then enter the ion trap 36 where they are then separated according to mass to charge ratios (m/z ratios). The figure shows the photon source 4 disposed in the ion trap 36. As discussed above, the photon source 4 may be disposed inside the ion trap 36 or adjacent to it. The photon source 4 is used for irradiating the ions and placing them in an excited state. This may occur in the ion trap or before the ion trap 36 depending upon the location of the photon source 4.

FIGS. 6 and 7 show similar methods as discussed above. However, the ions are produced in the ion source 3 after the sample is released from the GC column 30. The ions are then directed by the ion optics 32 toward the first mass spectrometer 20. The ions are then fragmented as discussed above and detected finally by detector 9.

Figure 8:
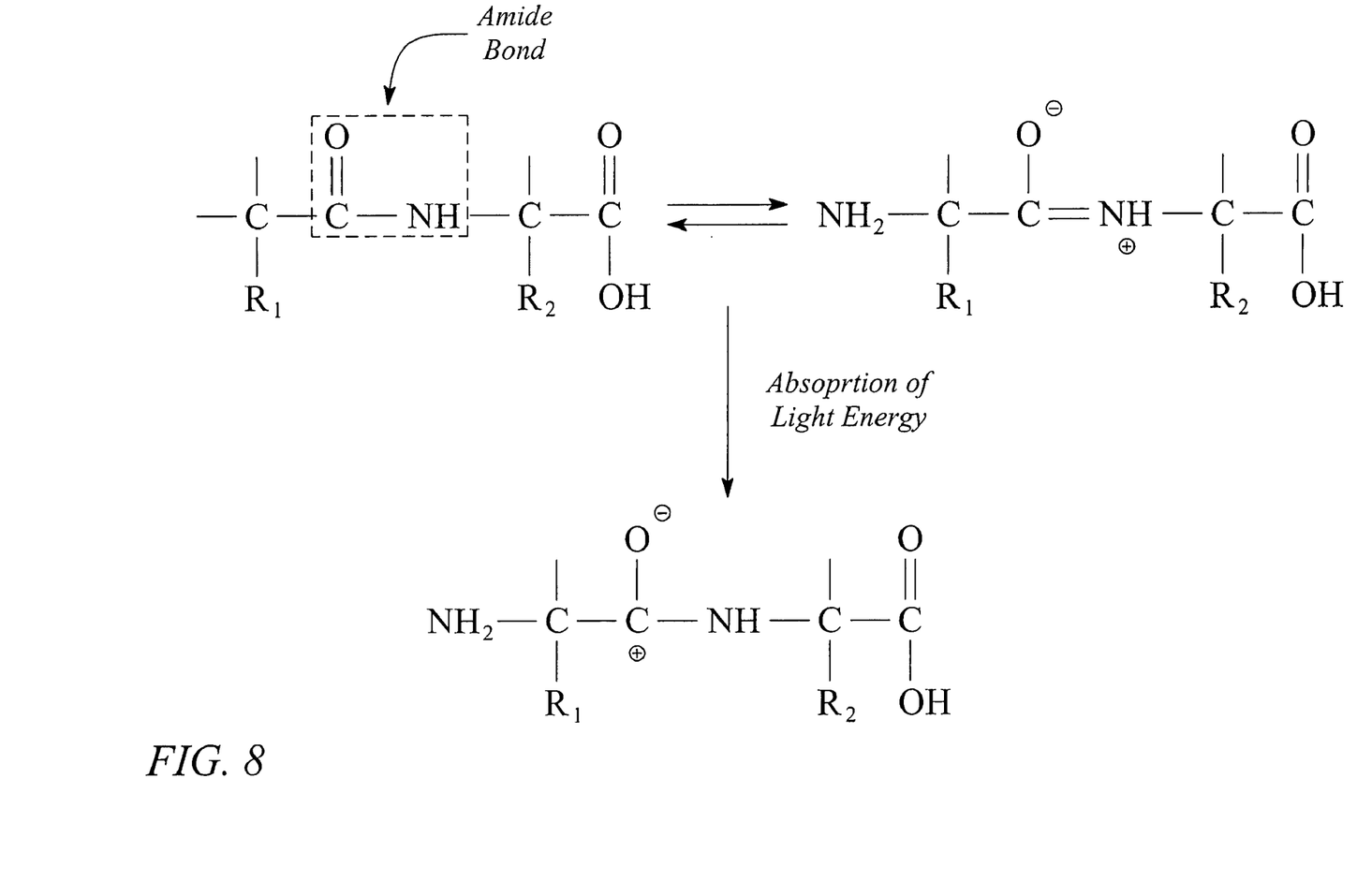
FIG. 8 shows a diagram of how peptide fragmentation might take place using the present invention.

FIG. 8 shows an example of a peptide and how the present technique would potentially fragment peptides. Ideally, peptide in (a), will adopt a resonance state (b) that will be subject to excitation as shown in (c). The collision with a collision gas or planar surface should provide for splitting of the molecule along the amide bond as shown in the diagram. The excitation and collision must be done in a fairly short time since the relaxation times of most molecules are fairly short. In other words, the molecules must reach an excited state and must be immediately collided with a gas or surface before they are allowed to relax to their non-excited states. This is ideal for peptide sequencing and determination due to the predictable fragmentations. It should also be noted that the present technique does not require multiply charges species and works in both the negative and positive ion modes. The technique can be used with molecules having single, double, aromatic and triple bonds. For instance, various molecules selected from the group consisting of a ketone, an amide, an aldehyde, an ester, an ether, an aromatic, a molecule having a double bond, a molecule having a triple bond, and a peptide may be employed. Other molecules or compounds not discussed or disclosed or having similar type properties may also be employed.

Figure 9:
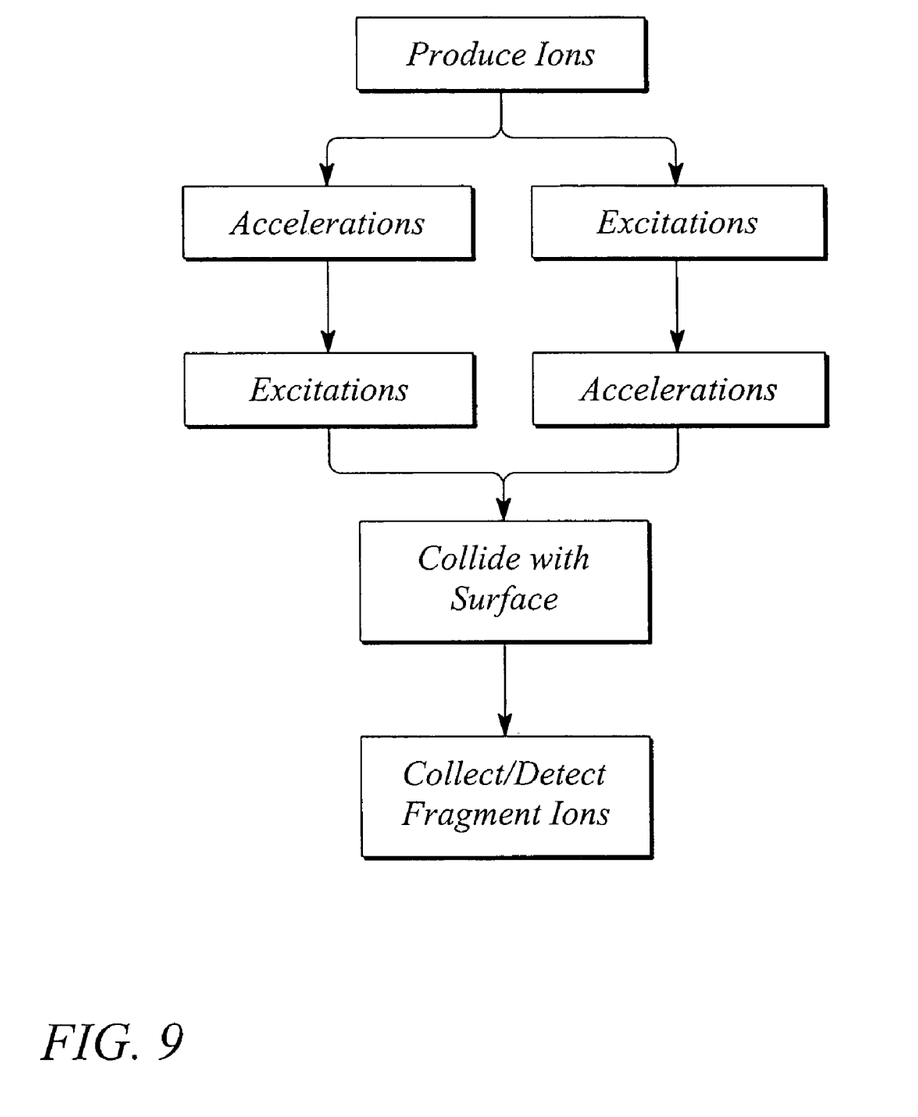
FIG. 9 shows a flow chart of the steps of the method of the present invention.

FIG. 9 shows a general flow chart of the method of the invention. Details of the explicit embodiments utilizing these principles are discussed in FIGS. 2-7.

We claim:

1. A device for photo-activated collision induced dissociation, comprising:
   (a) an ion source for producing ions;
   (b) a photon source adjacent to the ion source for photo-activating ions produced by the ion source; and
   (c) an electrical element adjacent to the photon source for creating an electric field for accelerating ions produced by the ion source and photo-activated by the photon source, wherein ions are produced by the ion source, photo-activated by the photon source and accelerated into a surface to cause dissociation of the activated ions.

2. A device as recited in claim 1, wherein the ion source is below atmospheric pressure.

3. A device as recited in claim 1, wherein the ion source is maintained at atmospheric pressure.

4. A device as recited in claim 1, further comprising a housing and wherein the ion source, photon source and electrical element are disposed in the housing.

5. A device as recited in claim 4, wherein the housing is maintained under vacuum.

6. A device as recited in claim 1, wherein the device further comprises a gas region that provides for dissociation.

7. A device as recited in claim 1, wherein the device comprises a portion of a collision cell of a Q-TOF.

8. A device as recited in claim 1, wherein the device comprises a portion of a triple quadrupole.

9. A device as recited in claim 1, wherein the surface comprises a portion of the device.

10. A device as recited in claim 1, wherein the surface comprises a portion of a gas molecule.

11. A device as recited in claim 1, wherein the ions produced comprise negative ions.

12. A device as recited in claim 1, wherein the ions produced comprise positive ions.

13. A device as recited in claim 1, wherein the ions produced comprise peptide ions.

14. A device as recited in claim 1, wherein the photon source comprises a UV lamp.

15. A device as recited in claim 1, wherein the photon source comprises a visible light lamp.

16. A device as recited in claim 1, wherein the photon source emits light in the wavelength of from 190-900 nm in wavelength.

17. A device as recited in claim 1, wherein the ion source comprises an AP-MALDI ion source.

18. A device as recited in claim 1, wherein the ion source comprises an EI ion source.

19. A device as recited in claim 1, wherein the ion source comprises a CI ion source.

20. A device as recited in claim 1, wherein the ion source comprise a MALDI ion source.

21. A device as recited in claim 1, wherein the ion source comprises an APPI ion source.

22. A device as recited in claim 1, wherein the electrical element comprises a portion of a capillary.

23. A device as recited in claim 1, wherein the electrical element has a voltage differential of about 0 to 1000 volts.

24. A mass spectrometry system for photo-activated dissociation, comprising:
   (a) an ion source for producing ions;
   (b) a photon source adjacent to the ion source for photo-activating ions produced by the ion source;

(c) an electrical element adjacent to the photon source for creating an electric field for accelerating ions produced by the ion source and photo-activated by the photon source, wherein ions are produced by the ion source, photo-activated by the photon source and accelerated into a surface to cause dissociation of the activated ions; and (d) a detector downstream from the ion source for detecting dissociated ions.

25. A mass spectrometry system as recited in claim 24, further comprising a housing.

26. A mass spectrometry system as recited in claim 25, wherein the housing is under vacuum.

27. A mass spectrometry system as recited in claim 24, wherein the surface comprises a portion of the device.

28. A mass spectrometry system as recited in claim 24, wherein the surface comprises a portion of a gas molecule.

29. A mass spectrometry system as recited in claim 24, wherein the photon source comprises a UV lamp.

30. A mass spectrometry system as recited in claim 24, wherein the photon source comprises a visible light lamp.

31. A mass spectrometry system as recited in claim 24, wherein the photon source emits light in the wavelength of from 190-900 nm in wavelength.

32. A mass spectrometry system as recited in claim 24, wherein the ion source comprises an AP-MALDI ion source.

33. A mass spectrometry system as recited in claim 24, wherein the ion source comprises an EI ion source.

34. A mass spectrometry system as recited in claim 24, wherein the ion source comprises a CI ion source.

35. A mass spectrometry system as recited in claim 24, wherein the ion source comprise a MALDI ion source.

36. A mass spectrometry system as recited in claim 24, wherein the ion source comprises an APPI ion source.

37. A mass spectrometry system as recited in claim 24, wherein the electrical element comprises an electrode.

38. A mass spectrometry system as recited in claim 24, wherein the electrical element has a voltage differential from 0 to 1000 volts.

39. A mass spectrometry system as recited in claim 24, wherein the detector comprises a Q-TOF.

40. A mass spectrometry system as recited in claim 24, wherein the detector comprises a time of flight detector.

41. A method for photoactivated dissociation, comprising:
(a) providing ions;
(b) photoactivating the ions to a higher energy state;
(c) accelerating the ions; and
(d) colliding the ions with a surface to cause them to dissociate at certain preferred bonds.

42. A method as recited in claim 41, wherein the ions are from peptides.

43. A method as recited in claim 41, wherein the surface comprises a portion of a gas molecule.

44. A method as recited in claim 41, wherein the surface comprises a portion of the device.

45. A device under vacuum for photo-activated collision induced dissociation, comprising:
(a) an ion source for producing ions to be photo-activated and induced for collision dissociation;
(b) a photon source adjacent to the ion source for photo-activating ions produced by the ion source;
(c) an electrical element adjacent to the photon source for creating an electric field for accelerating ions produced by the ion source and photo-activated by the photon source, wherein ions are produced by the ion source, photo-activated by the photon source and accelerated into a surface in a housing to cause collision induced dissociation of the activated ions.

* * * * *